United States Patent
Fankhauser

(10) Patent No.: US 11,203,729 B2
(45) Date of Patent: Dec. 21, 2021

(54) UNSATURATED MACROCYCLIC EPOXIDE AS PERFUMING INGREDIENT

(71) Applicant: FIRMENICH SA, Geneva (CH)

(72) Inventor: Peter Fankhauser, Meyrin (CH)

(73) Assignee: FIRMENICH SA, Geneva (CH)

( * ) Notice: Subject to any disclaimer, the term of this patent is extended or adjusted under 35 U.S.C. 154(b) by 147 days.

(21) Appl. No.: 16/109,102

(22) Filed: Aug. 22, 2018

(65) Prior Publication Data

US 2018/0362881 A1    Dec. 20, 2018

Related U.S. Application Data

(62) Division of application No. 15/305,686, filed as application No. PCT/EP2015/058435 on Apr. 17, 2015, now abandoned.

(30) Foreign Application Priority Data

Apr. 24, 2014 (EP) .................................... 14165739

(51) Int. Cl.
| | | |
|---|---|---|
| C11B 9/00 | (2006.01) | |
| A61L 9/01 | (2006.01) | |
| C11D 3/50 | (2006.01) | |
| A61L 2/00 | (2006.01) | |
| A61L 9/00 | (2006.01) | |
| A61K 8/49 | (2006.01) | |
| A61Q 13/00 | (2006.01) | |
| A61Q 15/00 | (2006.01) | |
| A61Q 19/00 | (2006.01) | |
| C11D 3/00 | (2006.01) | |

(52) U.S. Cl.
CPC .......... *C11B 9/0076* (2013.01); *A61K 8/4973* (2013.01); *A61L 2/00* (2013.01); *A61L 9/00* (2013.01); *A61L 9/01* (2013.01); *A61Q 13/00* (2013.01); *A61Q 15/00* (2013.01); *A61Q 19/002* (2013.01); *C11D 3/001* (2013.01); *C11D 3/50* (2013.01)

(58) Field of Classification Search
CPC ............................ C11B 9/0076; A61K 8/4973
See application file for complete search history.

(56) References Cited

U.S. PATENT DOCUMENTS

| 3,845,078 A | 10/1974 | Lemberg | |
| 7,528,268 B2 * | 5/2009 | Mimoun | ............ C07D 301/12 502/340 |

FOREIGN PATENT DOCUMENTS

| EP | 0 965 575 A1 | 12/1999 |
| EP | 1 170 291 A1 | 1/2002 |
| GB | 960305 A | 6/1964 |
| WO | 2004/078738 A1 | 9/2004 |
| WO | 2009/117498 A2 | 9/2009 |
| WO | 2012/175437 A1 | 12/2012 |
| WO | 2013/107673 A1 | 7/2013 |

OTHER PUBLICATIONS

International Search Report and Written Opinion, Appl. No. PCT/EP2015/058435, dated Jul. 7, 2015.
International Preliminary Report on Patentability, Appl. No. PCT/EP2015/058435, dated Oct. 25, 2016.
Balbolov et al., "Kinetics of hydrogenation of 1,2-epoxycyclododeca-5,9-diene on palladium catalysts," Journal of Molecular Catalysis, 68:95-103 (1991).
March's Advanced Organic Chemistry: Reactions, Mechanisms, and Structure, 5th Edition 2001, pp. 1051-1054.
Stumpf et al., "Epoxidierung von cis-und trans-Doppelbindungen in C12-Ring-Kohlenwasserstoffen," Justus Liebigs Annalen der Chemie, Verlag Chemie GmbH, 687:136-149 (1965) (German language).
U.S. Appl. No. 15/305,686, Non-Final Rejection dated Feb. 9, 2018.
U.S. Appl. No. 15/305,686, Final Rejection dated May 24, 2018.
U.S. Appl. No. 15/305,686, Advisory Action dated Aug. 15, 2018.

* cited by examiner

*Primary Examiner* — Arrie L Reuther
(74) *Attorney, Agent, or Firm* — Armstrong Teasdale LLP

(57) ABSTRACT

A method of use of a compound of formula (I)

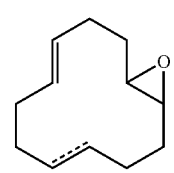

(I)

in the form of any one of its stereoisomers or a mixture thereof as a perfuming ingredient to impart to a perfuming composition or perfuming consumer product an odor note of woody, cedar/ambery character optionally having a thujonic aromatic character.

13 Claims, No Drawings

UNSATURATED MACROCYCLIC EPOXIDE AS PERFUMING INGREDIENT

CROSS-REFERENCE TO RELATED APPLICATIONS

This application is a division of U.S. patent application Ser. No. 15/305,686 filed Oct. 15, 2016, which is the 371 filing of International patent application no. PCT/EP2015/058435 filed Apr. 17, 2015, which claims the benefit of European patent application no. 14165739.5 filed Apr. 24, 2014.

TECHNICAL FIELD

The present invention relates to the field of perfumery. More particularly, it concerns a compound of formula (I), in the form of any one of its stereoisomers or of any mixture thereof, and its use as perfuming ingredient. Therefore, following what is mentioned herein, the present invention comprises the invention's compound as part of a perfuming composition or of a perfuming consumer product.

PRIOR ART

The compounds 13-oxabicyclo[10.1.0]trideca-4,8-diene and 13-oxabicyclo[10.1.0]tridec-4-ene are known as such and are respectively reported for example in WO 2012/175437 or in WO 2004/078738 and in GB 960305 or in *J. Mol. Catal.* 1991, 69 (1), 95-103. The prior art reports the invention's compound always as chemical products or as intermediates, but never discloses or suggests any organoleptic properties of the compound of formula (I), or any use of said compound in the field of perfumery.

The perfumery ingredient having the closest chemical structure is 1,4,8-trimethyl-13-oxabicyclo[10.1.0]trideca-4,8-diene (also known as Cedroxyde®, from Firmenich SA). However, said prior art compound not only differs from the present compound by at least three methyl groups, but is also differs by its olfactive properties. Such prior art compound does not suggest any organoleptic properties of the compound of formula (I), or any use of said compound in the field of perfumery.

DESCRIPTION OF THE INVENTION

We have now surprisingly discovered that a compound of formula (I)

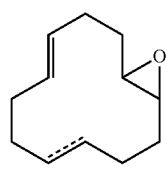

(I)

in the form of any one of its stereoisomers or of any mixture thereof and wherein the dotted line represents a carbon-carbon single or double bond;
can be used as perfuming ingredient, for instance to impart odor notes of the woody, cedar/ambery type and optionally also thujonic aromatic type.

For the sake of clarity, by the expression "wherein the dotted line represents a carbon-carbon single or double bond", or the similar, it is meant the normal meaning understood by a person skilled in the art, i.e. that the whole bonding (solid and dotted lines) between the carbon atoms connected by said dotted line is a carbon-carbon single or double bond.

The invention's compound possesses one or two carbon-carbon double bonds as well as two fused rings, and each of said moiety can have two different stereochemistries (e.g. E or Z; (RS;RS) or (RS,SR)), and the compound may even be chiral or not. Therefore the compound of formula (I) can be in the form of a composition of matter comprising, or consisting of, the various stereoisomers.

The invention's compound can be in a racemic form or enantioenriched (if chiral).

In particular, for compound of formula (I) wherein the dotted line represents a carbon-carbon double bond; i.e. compound of formula (I) having two carbon-carbon double bonds, each carbon-carbon double bond of said compound, independently from each other, can be in a configuration Z or E or a mixture thereof. For the sake of clarity, by the expression "each carbon-carbon double bond of said compound, independently from each other, can be in a configuration Z or E or a mixture thereof" it is meant also a composition of matter comprising the various (E,E), (E,Z), (Z,E) and (Z,Z) isomers. For compound of formula (I) wherein the dotted line represents a carbon-carbon single bond, the carbon-carbon double bond of said compound can be in a configuration Z or E or a mixture thereof.

The same applies to the epoxy moiety. The epoxy moiety can be in a configuration (1RS,12RS) or (1RS,12SR) or a mixture thereof. For the sake of clarity, by the expression "(1RS,12RS)" it is meant an equimolar mixture of (1R,12R) and (1S,12S) and by the expression "(1RS,12SR)" it is meant an equimolar mixture of (1R,12S) and (1S,12R). As non-limiting example one may cite the following stereoisomers: (1RS,4E,8Z,12RS)-13-oxabicyclo[10.1.0]trideca-4,8-diene or (1RS,4E,8E,12RS)-13-oxabicyclo[10.1.0]trideca-4,8-diene.

In other words, said compound (I) can be in the form of an essentially pure stereoisomer (i.e. the (1RS,4E,8Z,12RS) one) or in the form of a composition of matter comprising several stereoisomers, e.g. in a mixture comprising the stereoisomers (4E,8E), (4Z,8E) and (4E,8Z) in various w/w ratio.

According to a preferred embodiment, the compound of formula (I) is 13-oxabicyclo[10.1.0]trideca-4,8-diene (wherein the dotted line represents a carbon-carbon double bond).

According to any embodiment, the compound of formula (I), in particular in the form of a mixture of stereoisomers, can also be better defined by the process for obtaining it. Indeed, the compound of formula (I) is obtainable by the process comprising the step of treating cyclododaca-1,5,9-triene in the form of any one of its stereoisomers or of any mixture thereof with an epoxidizing agent and optionally monohydrogenating one double bond.

Cyclododeca-1,5,9-triene, a known and commercially product, possesses 3 carbon-carbon double bonds which can have different stereochemistries (i.e. can be in an E or Z configuration).

According to any one of the above embodiments of the invention, cyclododeca-1,5,9-triene is in the form of a mixture of isomers (1E,5E,9E), (1Z,5E,9E) and (1Z,5Z,9E).

According to a preferred embodiment, cyclododaca-1,5,9-triene is in the form of a mixture of isomer (1Z,5E,9E) and isomer (1E,5E,9E) comprising at least 90% w/w of the isomer (1Z,5E,9E), most preferably comprising at least 95% w/w of the isomer (1Z,5E,9E), even more preferably comprising at least 98% w/w of the isomer (1Z,5E,9E), the rest being the isomer (1E,5E,9E). Cyclododaca-1,5,9-triene in a form of a mixture comprising at least 98% of isomer (1Z,5E,9E) and at most 2% of isomer (1E,5E,9E), also here-referred as compound (II-a), are commercially available from Evonik Industries.

According to a particular embodiment, cyclododeca-1,5,9-triene is in the form of a mixture comprising at least 95% w/w of the isomer (1E,5E,9E) also here-referred as compound (II-c) which is commercially available from Sigma-Aldrich Co.

According to another particular embodiment, cyclododaca-1,5,9-triene is in the form of a mixture comprising at least 30% w/w of the isomer (1Z,5E,9E), at most 75% w/w of the isomer (1E,5E,9E) and at most 5% w/w of the isomer (1Z,5Z,9E), also here-referred as compound (II-b). An isomerization of the commercially available (1Z,5E,9E)-cyclododaca-1,5,9-triene allows to increase the proportion of isomer (1E,4E,8E). The person skilled in the art is well aware of isomerization conditions reported in the literature and will be able to select the best conditions in order to obtain the desired isomeric mixture. Moreover, the person skilled in the art is able to mix the commercially available quality of cyclododecatriene in order to obtain a cyclodo-decatriene in the desired form of mixture of isomers.

For the sake of clarity, by the term "epoxidizing agent" and similar, it is meant the normal meaning in the art, i.e. a reactant able to react with a double bond to form an epoxide. Specific, and non-limiting, examples of epoxidizing agent is selected from the group consisting of $C_{2-8}$ peroxy acids, such as peracetic acid, ethaneperoxoic acid, buthaneperoxoic acid, 2-ethylhexaneperoxoic acid, butanediperoxoic acid, perbenzoic acid, para-methylperbenzoic acid, methoxyperbenzoic acid, meta-chloroperbenzoic acid, para-chloroperbenzoic acid or ortho-chloroperbenzoic acid, hydrogen peroxide, dioxygen, alkyl peroxide such as tert-butylhydroperoxide and a mixture thereof. The reaction is optionally catalyzed by a transitional metal. An overview of epoxydation condition could be found in March's "Advanced Organic Chemistry", $5^{th}$ edition 2001, pg 1051-1054). The person skilled in the art is able to select the most appropriate epoxidizing agent.

As a person skilled in the art knows, said epoxidizing agent can be in a pure form or diluted in a solvent. Typically it can be used an aqueous solution having a concentration ranging from 10% to 50% w/w, preferably between 30% and 40%, the % being relative to the total weight of the solution. However other solvent can be used, such a $C_{1-10}$ carboxylic acid (preferably the corresponding carboxylic acid, i.e. acetic acid in case of peracetic acid), a $C_{6-10}$ alkane or cycloalkane, a $C_{3-10}$ ester.

According to any embodiment of the invention, said epoxidizing agent is selected amongst the solutions containing between 10% to 50% w/w, preferably between 30% and 40%, the % being relative to the total weight of the solution, of a $C_{2-8}$ peroxy acid.

For the sake of clarity, by the term "monohydrogenating one double bond", it is meant the normal meaning in the art, i.e. the selective hydrogenation of one double bond. This reaction is well known in the art, and the person skilled in the art will be able to select the appropriate condition in odor to hydrogenate mainly one double bond.

Without being bound by theory, we believe that the invention's compound obtainable by such a process is in the form of a composition of matter comprising predominantly (i.e. at least 90% w/w) the following stereoisomers:

(1RS,4E,8E,12RS)-13-oxabicyclo[10.1.0]trideca-4,8-diene (also referred to as isomer (A));
(1RS,4E,8E,12SR)-13-oxabicyclo[10.1.0]trideca-4,8-diene (also referred to as isomer (B));
(1RS,4E,8Z,12RS)-13-oxabicyclo[10.1.0]trideca-4,8-diene (also referred to as isomer (C)).

According to a particular embodiment of the invention, said compound (I) is in the form of a composition of matter comprising essentially, or even consisting of, the isomers (A), (B) and (C) in the following weight %:
(A) being comprised between 0% and 5%, preferably between 0% and 3%;
(B) being comprised between 5% and 30%, preferably between 7% and 22%; and
(C) being comprised between 65% and 90%, preferably between 72% and 85%.

Alternatively, according to a particular embodiment of the invention, said compound (I) is in the form of a composition of matter comprising essentially, or even consisting of, the isomers (A), (B) and (C) in the following weight %:
(A) being comprised between 50% and 75%, preferably between 60% and 70%;
(B) being comprised between 0% and 5%, preferably between 0% and 3%; and
(C) being comprised between 20% and 50%, preferably between 27% and 40%.

According to a particular embodiment of the invention, said compound (I) is in the form of a composition of matter comprising essentially, or even consisting of, the isomers (A), (B) and (C) in the following weight ratio:
(A)/(C)/(B)=1/80/19 (also referred to as compound (I-a)) obtainable from epoxydation of compound (II-a);
(A)/(C)/(B)=63/36/1 (also referred to as compound (I-b)) obtainable from epoxydation of compound (II-b); or
(A)/((C)+(B))=99/1 (also referred to as compound (I-c)) obtainable from epoxydation of compound (II-c).

For the sake of clarity, by the expression "comprising essentially" it is meant at least 80% w/w, or even 90% w/w, of the composition is made of the listed materials.

As specific examples of the invention's compound, one may cite, as non-limiting example, the compound (I-a). Said compound has a unique odor having a duality characterized by a fresh top note woody, aromatic type of reminiscent of thuja leaves and a middle, bottom note of the woody cedar/ambery type as well as a slightly earthy aspect. The presence of such fresh, raising top note of the woody, aromatic type is an exceptional feature of said invention's compound, since in general the woody notes are associated with middle to bottom notes. The overall olfactive impression of said compound is a very natural, raising and impact woody note which marries perfectly with the classical woody notes used in the art of perfumery.

Said compound (I-a) represents a particularly appreciated embodiment of the invention.

When the odor of the invention's compound is compared with that of the prior art compounds, e.g. Cedroxyde®, then the invention's compound distinguishes themselves by having an aromatic note and as well as being by having a clear top note contribution, all aspect which are absent in the prior art compound(s). Said differences lend the invention's compound and the prior art compound(s) to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. which does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

According to any one of the invention's embodiments, said perfuming composition can be one wherein the perfumery base comprises, or consists of, ingredients currently used to impart woody notes. Such ingredients imparting woody notes are well known to a person skilled in the art and can be easily retrieved in any perfumery text book or pertinent literature (e.g. the Arctander book cited above, or in the patent literature). Although an exhaustive list of such ingredients imparting woody notes would impossible, one may cite as non-limiting examples the following ones:
methyl cedryl ketone, Vertofix® (trademark owned by International Flavors &Fragrances, USA, 1-(octahydro-2,3,8,8-tetramethyl-2-naphthalenyl)-1-ethanone, Iso E Super®, Cedar oil, patchouli oil, cypriol oil, trans-1-(2,2,6-trimethyl-1-cyclohexyl)-3-hexanol, Norlimbanol®, 1-(2,2,3,6-tetramethyl-cyclohexyl)-3-hexanol, Limbanol®, (1'R,E)-2-ethyl-4-(2',2',3'-trimethyl-3'-cyclopenten-1'-yl)-2-buten-1-ol, 3,3-dimethyl-5-(2,2,3-trimethyl-3-cyclopenten-1-yl)-4-penten-2-ol, 2-ethyl-4-(2,2,3-trimethyl-3-cyclopenten-1-yl)-2-buten-1-ol, 5,5,9,13-tetramethyl-14,16-dioxatetracyclo[11.2.1.0(1,10).0(4,9)]hexadecane, {1-methyl-2-[(1',2',2'-trimethylbicyclo[3.1.0]hex-3'-yl)methyl]cyclopropyl}methanol, 3-methyl-5-(2,2,3-trimethyl-3-cyclopenten-1-yl)-4-penten-2-ol, (1R,3 S,7R,8R,10S,13R)-5,5,7,9,9,913-hexamethyl-4,6-dioxatetracyclo[6.5.1.0(1,10).0(3,7)]tetradecane, Ambrocenide® (trademark owned by Symrise AG, Germany) perhydro-2,6,6,7,8,8-hexamethylindeno[4,5-b]furan, Trisamber®, 2-(2,2,7,7-tetramethyl-tricyclo[6.2.1.0(1,6)]undec-4/5-en-5-yl)-1-propanol, Ambermax® (trademark owned by Givaudan SA, Switzerland), Casmirone® and 4,8-cyclododecadien-1-one.

In such embodiment, the invention's compound can be used in amounts comprised between about 5% to 50% w/w, relative to the total amount of ingredients imparting woody notes.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound. For the sake of clarity, said perfuming consumer product is a non-edible product.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer products may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compound according to the invention can be incorporated into the various aforementioned articles or compositions vary within a wide range of values. These values are dependent on the nature of the article to be perfumed and on the desired organoleptic effect as well as the nature of the co-ingredients in a given base when the compound according to the invention are mixed with perfuming co-ingredients, solvents or additives commonly used in the art.

For example, in the case of perfuming compositions, typical concentrations are in the order of 0.001% to 30% by weight, or even more, of the compound of the invention based on the weight of the composition into which they are incorporated. Concentrations lower than these, such as in the order of 0.01% to 10% by weight, can be used when these compounds are incorporated into perfumed articles, percentage being relative to the weight of the article.

The invention's compound can be prepared from cyclododecatriene according to a method as described herein-below in the Examples or as described in WO2009117498, EP1170291, WO2004078738, EP0965575, WO2012175437 and J. Mol. Catal. 1991, 69 (1), 95-103.

EXAMPLES

The invention will now be described in further detail by way of the following examples, wherein the abbreviations have the usual meaning in the art, the temperatures are indicated in degrees centigrade (° C.).

Example 1

Preparation of Compound of Formula (I)

To a mixture of sodium carbonate (160 g, 1.23 mol, 2.9 equiv.) in toluene (1000 mL) was added cyclododeca-1,5,9-triene (II-a) (500 g, 3.1 mol, 1 equiv.). The mixture was cooled down to 0° C. and peracetic acid (1000 mL, 3.9 mol, 1 equiv.)) was added dropwise over a 5 min-period. The reaction mixture was slowly warm to room temperature and stirred overnight. Then, the reaction mixture was cooled down to 0° C. and was poured onto an aqueous solution of $NaHSO_3$. The organic layer was washed with an aqueous solution of $NaHCO_3$ then with water and finally with brine. The combined organic extracts were dried over sodium sulfate and the solvent was evaporated. The residue was purified by distillation under reduced pressure (0.07 mbar, 110° C.) to provide a stereoisomers mixture of 13-oxabicyclo[10.1.0]trideca-4,8-diene. Based on analysis, the stereoisomers mixtures consists of 80% of (1RS,4E,8Z,12RS)-13-oxabicyclo[10.1.0]trideca-4,8-diene, 19% of (1RS,4E,8E,12SR)-13-oxabicyclo[10.1.0]trideca-4,8-diene and 1% of (1RS,4E,8E,12RS)-13-oxabicyclo[10.1.0]trideca-4,8-diene.

Example 2

Preparation of a Perfuming Composition

A perfuming composition for masculine cologne was prepared by admixing the following ingredients:

| Parts by weight | Ingredient |
| --- | --- |
| 50 | 10%* C 10 aldehyde |
| 20 | Ambrettolide ® [1)] |
| 100 | Ambrox ® [2)] |
| 10 | Amione ® [3)] |
| 50 | Bergamot essential oil |
| 120 | (Ethoxymethoxy)cyclododecane |
| 50 | 10%* Calone ® [4)] |
| 10 | Cardamon essential oil |
| 40 | Cashmeran ® [5)] |

-continued

| Parts by weight | Ingredient |
|---|---|
| 70 | 8-Methoxy-2,6,6,8-tetramethyl-tricyclo[5.3.1.0(1,5)]undecane |
| 20 | Coumarine |
| 10 | Cypress oil |
| 400 | Dihydromyrcenol |
| 700 | Exaltolide® [6] |
| 100 | 2-Methyl-4-(2,2,3-trimethyl-3-cyclopenten-1-yl)-4-penten-1-ol |
| 2000 | Habanolide® [7] |
| 1000 | Hedione® [8] HC |
| 250 | 3-(1,3-Benzodioxol-5-yl)-2-methylpropanal |
| 500 | Helvetolide® [9] |
| 40 | Hivernal® [10] |
| 400 | Hydroxycitronellal |
| 1600 | Iso E® [11] Super |
| 200 | Lyral® [12] |
| 300 | Mandarin essential oil |
| 70 | Crystal moss |
| 250 | Muscenone® [13] Delta |
| 30 | Myrrhone® [14] |
| 20 | Cis-3-Hexenol |
| 80 | Orange essential oil |
| 50 | 1%* 2,6,6-Trimethyl-1,3-cyclohexadiene-1-carbaldehyde |
| 40 | Amyl salicylate |
| 60 | Salicynile® [15] |
| 40 | 10%* Vanilline |
| 700 | Vertofix® [16] Coeur |
| 20 | Ionone Beta |
| 100 | Vulcanolide® [17] |
| 9500 | |

*in dipropyleneglycol
** in isopropyle myristate
[1] 16-hexadecanolide [a]
[2] (−)-(8R)-8,12-epoxy-13,14,15,16-tetranorlabdane [a]
[3] allyl ionone [b]
[4] 7-methyl-2H,4H-1,5-benzodioxepin-3-one [a]
[5] 1,2,3,5,6,7-hexahydro-1,1,2,3,3-pentamethyl-4-indenone [c]
[6] pentadecanolide [a]
[7] pentadecenolide [a]
[8] methyl cis-dihydrojasmonate [a]
[9] (1S,1'R)-2-[1-(3',3'-dimethyl-1'-cyclohexyl)ethoxy]-2-methylpropyl propanoate [a]
[10] 3-(3/1,1-dimethyl-5-indanyl)propanal [a]
[11] 1-(octahydro-2,3,8,8-tetramethyl-2-naphthalenyl)-1-ethanone [c]
[12] 4/3-(4-hydroxy-4-methylpentyl)-3-cyclohexene-1-carbaldehyde [c]
[13] 3-methyl-5-cyclopentadecen-1-one [a]
[14] 4-(2,2,C-3,T-6-tetramethyl-R-1-cyclohexyl)-3-buten-2-one [a]
[15] (2Z)-2-phenyl-2-hexenenitrile [a]
[16] methyl cedryl ketone [c]
[17] trans-5,6,7,8-tetrahydro-3,5,5,6,7,8,8-heptamethyl-2-naphthalenecarbaldehyde [a]
[a] origin: Firmenich SA, Geneva, Switzerland
[b] origin: Givaudan-Roure SA, Vernier, Switzerland
[c] origin: International Flavors & Fragrances, USA The addition of 500 parts by weight of Compound (I-a) to the above-described cologne imparted to the latter an amazing woody, aromatic top note, completing and complementary to the note imparted by Iso ER Super (which impact essentially the bottom notes).

The addition of the same amount of Cedroxyde® provided a different effect, devoid of the woody top note, as well as of the aromatic effect.

Example 3

Preparation of a Perfuming Composition

A perfuming composition for a detergent was prepared by admixing the following ingredients:

| Parts by weight | Ingredient |
|---|---|
| 150 | 1-Methyl-1-phenylethyl acetate |
| 1000 | Hexylcinnamic aldehyde |
| 20 | 9-Undecenal |
| 10 | Methyl anthranilate |
| 150 | Benzyl benzoate |
| 50 | 10%* Raspberry ketone |
| 750 | Citronellol |
| 80 | Citronellyl nitrile |
| 200 | Clearwood™ [1] |
| 50 | 10%* Ethyl (2e,4z)-2,4-decadienoate |
| 10 | Estragole |
| 50 | 10%* Ethylvanilline |
| 60 | Ethyl tricyclo[5.2.1.0.(2,6)]decane-2-carboxylate |
| 1000 | 70%** Galaxolide® [2] |
| 500 | Habanolide® [3] |
| 400 | Hedione® [4] |
| 60 | 10%* Indocolore™ [5] |
| 300 | Alpha iso methylionone |
| 1000 | Lilial® [6] |
| 500 | Linalool |
| 800 | Lorysia® [7] |
| 30 | 10%* 2-Ethyl methylbutyrate |
| 50 | Methylnaphthylketone |
| 150 | Muscenone® [8] Delta |
| 60 | 50%** Natactone™ [9] |
| 600 | Phenethylol |
| 800 | Orange essential oil |
| 200 | Wardia® [10] |
| 500 | Terpineol |
| 50 | 10%* Vanilline |
| 100 | Ylang oil |
| 20 | 2,4-Dimethyl-3-cyclohexene-1-carbaldehyde |
| 9700 | |

*in dipropyleneglycol
**in isopropyle myristate
[1] terpenic fraction of Patchouli oil, obtained by fermentation of sugars [a]
[2] 1,3,4,6,7,8-hexahydro-4,6,6,7,8,8-hexamethyl-cyclopenta-g-2-benzopyrane [c]
[3] pentadecenolide [a]
[4] methyl cis-dihydrojasmonate [a]
[5] 1-phenylvinyl acetate [a]
[6] 3-(4-tert-butylphenyl)-2-methylpropanal [b]
[7] 4-(1,1-dimethylethyl)-1-cyclohexyl acetate [a]
[8] 3-methyl-5-cyclopentadecen-1-one [a]
[9] (6R)-perhydro-3,6-dimethyl-benzo[b]furan-2-one [a]
[10] compounded perfumery base [a]
[a] origin: Firmenich SA, Geneva, Switzerland
[b] origin: Givaudan-Roure SA, Vernier, Switzerland
[c] origin: International Flavors & Fragrances, USA The addition of 300 parts by weight of Compound (I-a) to the above-described composition imparted to the latter an amazing woody, ambery and aromatic top note, completing and complementary to the Patchouli note imparted by Clearwood™ (which impact essentially the bottom notes).

The addition of the same amount of Cedroxyde® provided a different effect, devoid of the woody top note, as well as of the aromatic effect.

What is claimed is:

1. A method of use of a compound of formula (I) as a perfuming ingredient to confer, enhance, improve or modify the odor properties of a perfuming composition or of a perfumed article, which method of use comprises adding to said composition or article an effective amount of at least one compound of the perfuming ingredient, wherein formula (I) is:

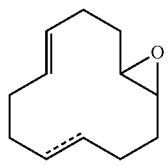

in the form of a composition of matter comprising the following stereoisomers in the following weight %:
- (1RS,4E,8E,12RS)-13-oxabicyclo[10.1.0]trideca-4,8-diene, also referred to as isomer (A), being comprised between 0% and 5%;
- (1RS,4E,8E,12SR)-13-oxabicyclo[10.1.0]trideca-4,8-diene, also referred to as isomer (B), being comprised between 5% and 30%; and
- (1RS,4E,8Z,12RS)-13-oxabicyclo[10.1.0]trideca-4,8-diene, also referred to as isomer (C), being comprised between 65% and 95%; and wherein the dotted line represents a carbon-carbon single or double bond, and wherein the perfuming ingredient imparts an odor note of woody, cedar/ambery character optionally having a thujonic aromatic character.

2. The method of claim 1, wherein the compound of formula (I) is in the form of a composition of matter comprising the isomers (A), (B) and (C) in the following weight %:
- (A) being comprised between 0% and 3%;
- (B) being comprised between 7% and 22%; and
- (C) being comprised between 72% and 85%.

3. The method of claim 1, wherein the compound of formula (I) is in the form of a composition of matter comprising the isomers (A), (B) and (C) in the following weight ratio:
- (A)/(C)/(B)=1/80/19 obtained from epoxydation of compound (II-a),
- wherein the compound (II-a) is cyclododeca-1,5,9-triene in a form of a mixture comprising at least 98% of isomer (1Z,5E,9E) and at most 2% of isomer (1E,5E,9E).

4. The method of claim 1, wherein the compound of formula (I) is obtained from a process which comprises treating cyclododeca-1,5,9-triene in the form of any one of its stereoisomers or of any mixture thereof with an epoxidizing agent and optionally monohydrogenating one double bond.

5. The method of claim 4, wherein the cyclododeca-1,5,9-triene is compound (II-a), compound (II-b), or compound (II-c), wherein the compound (II-a) is cyclododeca-1,5,9-triene in a form of a mixture comprising at least 98% of isomer (1Z,5E,9E) and at most 2% of isomer (1E,5E,9E); wherein the compound (II-b) is cyclododeca-1,5,9-triene in the form of a mixture comprising at least 30% w/w of the isomer (1Z,5E,9E), at most 75% w/w of the isomer (1E,5E,9E) and at most 5% w/w of the isomer (1Z,5Z,9E); wherein the compound (II-c) is cyclododeca-1,5,9-triene in the form of a mixture comprising at least 95% w/w of the isomer (1E,5E,9E).

6. A perfuming composition comprising:
i) at least one compound of formula (I) as a perfuming ingredient
ii) at least one ingredient selected from the group consisting of a perfumery carrier and a perfumery base; and
iii) optionally at least one perfumery adjuvant;
wherein formula (I) is:

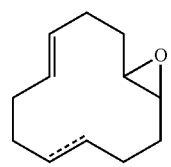

in the form of a composition of matter comprising the following stereoisomers in the following weight %:
- (1RS,4E,8E,12RS)-13-oxabicyclo[10.1.0]trideca-4,8-diene, also referred to as isomer (A), being comprised between 0% and 5%;
- (1RS,4E,8E,12SR)-13-oxabicyclo[10.1.0]trideca-4,8-diene, also referred to as isomer (B), being comprised between 5% and 30%; and
- (1RS,4E,8Z,12RS)-13-oxabicyclo[10.1.0]trideca-4,8-diene, also referred to as isomer (C), being comprised between 65% and 95%; and wherein the dotted line represents a carbon-carbon single or double bond, and wherein the perfuming ingredient imparts an odor note of woody, cedar/ambery character optionally having a thujonic aromatic character.

7. The perfuming composition of claim 6, wherein the compound (I) is in the form of a composition of matter comprising the isomers (A), (B) and (C) in the following weight %:
- (A) being comprised between 0% and 3%;
- (B) being comprised between 7% and 22%; and
- (C) being comprised between 72% and 85%.

8. The perfuming composition of claim 6, wherein the compound (I) is in the form of a composition of matter comprising the isomers (A), (B) and (C) in the following weight ratio:
- (A)/(C)/(B)=1/80/19 obtained from epoxydation of compound (II-a),
- wherein the compound (II-a) is cyclododeca-1,5,9-triene in a form of a mixture comprising at least 98% of isomer (1Z,5E,9E) and at most 2% of isomer (1E,5E,9E).

9. A perfuming consumer product comprising at least one compound of formula (I) as a perfuming ingredient, wherein formula (I) is:

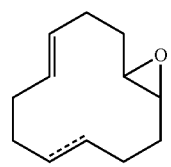

in the form of a composition of matter comprising the following stereoisomers in the following weight %:

(1RS,4E,8E,12RS)-13-oxabicyclo[10.1.0]trideca-4,8-diene, also referred to as isomer (A), being comprised between 0% and 5%;

(1RS,4E,8E,12SR)-13-oxabicyclo[10.1.0]trideca-4,8-diene, also referred to as isomer (B), being comprised between 5% and 30%; and (1RS,4E,8Z,12RS)-13-oxabicyclo[10.1.0]trideca-4,8-diene, also referred to as isomer (C), being comprised between 65% and 95%; and wherein the dotted line represents a carbon-carbon single or double bond, and wherein the perfuming ingredient imparts an odor note of woody, cedar/ambery character optionally having a thujonic aromatic character.

10. A perfuming consumer product according to claim 9, wherein the perfuming consumer product is a perfume, a fabric care product, a body-care product, an air care product or a home care product.

11. A perfuming consumer product according to claim 9, wherein the perfuming consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

12. The perfuming consumer product of claim 11, wherein the compound (I) is in the form of a composition of matter comprising the isomers (A), (B) and (C) in the following weight %:

(A) being comprised between 0% and 3%;
(B) being comprised between 7% and 22%; and
(C) being comprised between 72% and 85%.

13. The perfuming consumer product of claim 11, wherein the compound (I) is in the form of a composition of matter comprising the isomers (A), (B) and (C) in the following weight ratio:

(A)/(C)/(B)=1/80/19 obtained from epoxydation of compound (II-a), wherein the compound (II-a) is cyclododeca-1,5,9-triene in a form of a mixture comprising at least 98% of isomer (1Z,5E,9E) and at most 2% of isomer (1E,5E,9E).

* * * * *